US007875708B2

(12) United States Patent  
Jain et al.

(10) Patent No.: US 7,875,708 B2
(45) Date of Patent: Jan. 25, 2011

(54) SIALIC ACID DERIVATIVES

(75) Inventors: Sanjay Jain, London (GB); Ioannis Papaioannou, London (GB); Smita Thobhani, London (GB)

(73) Assignee: Lipoxen Technologies Limited, London (GB)

( * ) Notice: Subject to any disclaimer, the term of this patent is extended or adjusted under 35 U.S.C. 154(b) by 864 days.

(21) Appl. No.: 11/660,128

(22) PCT Filed: Aug. 12, 2005

(86) PCT No.: PCT/GB2005/003160

§ 371 (c)(1),
(2), (4) Date: Jul. 13, 2007

(87) PCT Pub. No.: WO2006/016168

PCT Pub. Date: Feb. 16, 2006

(65) Prior Publication Data

US 2007/0282096 A1    Dec. 6, 2007

(30) Foreign Application Priority Data

Aug. 12, 2004  (WO) .............. PCT/GB2004/003488
Feb. 23, 2005  (EP) ................................. 05251015

(51) Int. Cl.
*C07H 15/26* (2006.01)
*C07H 1/00* (2006.01)
(52) U.S. Cl. .................. 536/17.2; 536/18.5; 536/18.6
(58) Field of Classification Search ............... 536/17.2, 536/18.5, 18.6
See application file for complete search history.

(56) References Cited

U.S. PATENT DOCUMENTS 5,405,753 A    4/1995  Brossmer et al.
5,846,951 A   12/1998  Gregoriadis

FOREIGN PATENT DOCUMENTS

| EP | 0 747 063 | 11/1996 |
| WO | WO-91/14697 | 10/1991 |
| WO | WO-01/87922 | 11/2001 |
| WO | WO-2005/016973 | 2/2005 |

OTHER PUBLICATIONS

Lee et al, Analytical Biochemistry, 1994, 216, 358-364.*
Bayer et al, Analytical Biochemistry, 1988, 170, 271-181.*
International Search Report for PCT/GB2005/003160, mailed on Mar. 21, 2006, 5 pages.
Schwarz et al., Nuclear Medicine and Biology (1999) 26(4):383-388.
Bendele et al., Toxicological Sciences (1998) 42:152-157.
Beranova et al., Biomaterials (2000) 11:521-524.
Brocchini, Drug Discovery Today (2003) 8:111-112.
Carlsson et al., Biochem. Journal (1978) 173:723-737.
Cheng et al., Bioconjugate Chemistry (1999) 10:520-528.
Cho and Troy, PNAS USA (1994) 91:11427-11431.
Conover et al., Artificial Organ (1997) 21:369-378.
Dyer, Methods of Biochemical Analysis (1956) 3:111-152.
Fernandes and Gregoriadis, Biochimica et Biophysica Acta (1996) 1293:90-96.
Fernandes and Gregoriadis, Biochimica et Biophysica Acta (1997) 1341:26-34.
Fleury and Lange, Comptes Rendus Academic Sciences (1932) 195:1395-1397.
Gregoriadis, "Drug and vaccine delivery systems" in PharmaTech, World Markets Research Centre Limited, London (2001) 172-176.
Gregoriadis et al., FEBS Letters (1993) 315:271-276.
Gregoriadis et al., "Polysialic Acids: Potential for long circulating drug, protein, liposome and other microparticle constructs" in Targeting of Drugs, Stealth Therapeutic Systems, Gregoriadis and McCormack, (eds.), Plenum Press (1998) pp. 193-205.
Gregoriadis et al., Cellular and Molecular Life Sciences (2000) 57:1964-1969.
Hreczuk-Hirst et al., Preparation and properties of polysialylated interferon-α-2b, AAPS Annual Meeting, (2002) Toronto, Canada, M1056.
Hunter and Moghimi, Drug Discovery Today (2002) 7:998-1001.
Jain et al., Biochimica et Biophysica Acta (2003) 1622:42-49.
Jain et al., Drug Delivery Systems and Sciences (2004) 4(2):3-9.
Jennings and Lugowski, Journal of Immunology (1981) 127:1011-1018.
Lifely et al., Carbohydrate Research (1981) 94:193-203.
Molineux, Curr. Pharm. Des. (2004) 10(11):1235-1244.
Muflenhoff et al., Current Opinions in Structural Biology (1998) 8:558-564.
Park and Johnson, The Journal of Biological Chemistry (1949) 149-151.
Rutishauser, Polysialic Acid as a Regulator of Cell Interactions, Chapter 12, pp. 367-382 (1989).
Satake et al., The Journal of Biochemistry (1960) 47(5):654-660.
Svennerholm, Biochimica et Biophysica Acta (1957) 24:604-611.
Troy, Trends in Glycoscience and Glycotechnoogy (1990) 2:430-449.
Troy, Glycobiology (1992) 2(1):5-23.
Wang, International Journal of Pharmaceutics (1999) 185:129-188.

* cited by examiner

*Primary Examiner*—Shaojia Anna Jiang
*Assistant Examiner*—Ganapathy Krishnan
(74) *Attorney, Agent, or Firm*—Morrison & Foerster LLP

(57) ABSTRACT

An amine or hydrazide derivative of a sialic acid unit, e.g. in a polysaccharide, is reacted with a bifunctional reagent at least one of the functionalities of which is an ester of N-hydroxy succinimide, to form an amide or hydrazide product. The product has a useful functionality, which allows it to be conjugated, for instance to proteins, drugs, drug delivery systems or the like. The process is of particular utility for derivatising amine groups introduced in sialic acid terminal groups of polysialic acids.

5 Claims, 15 Drawing Sheets

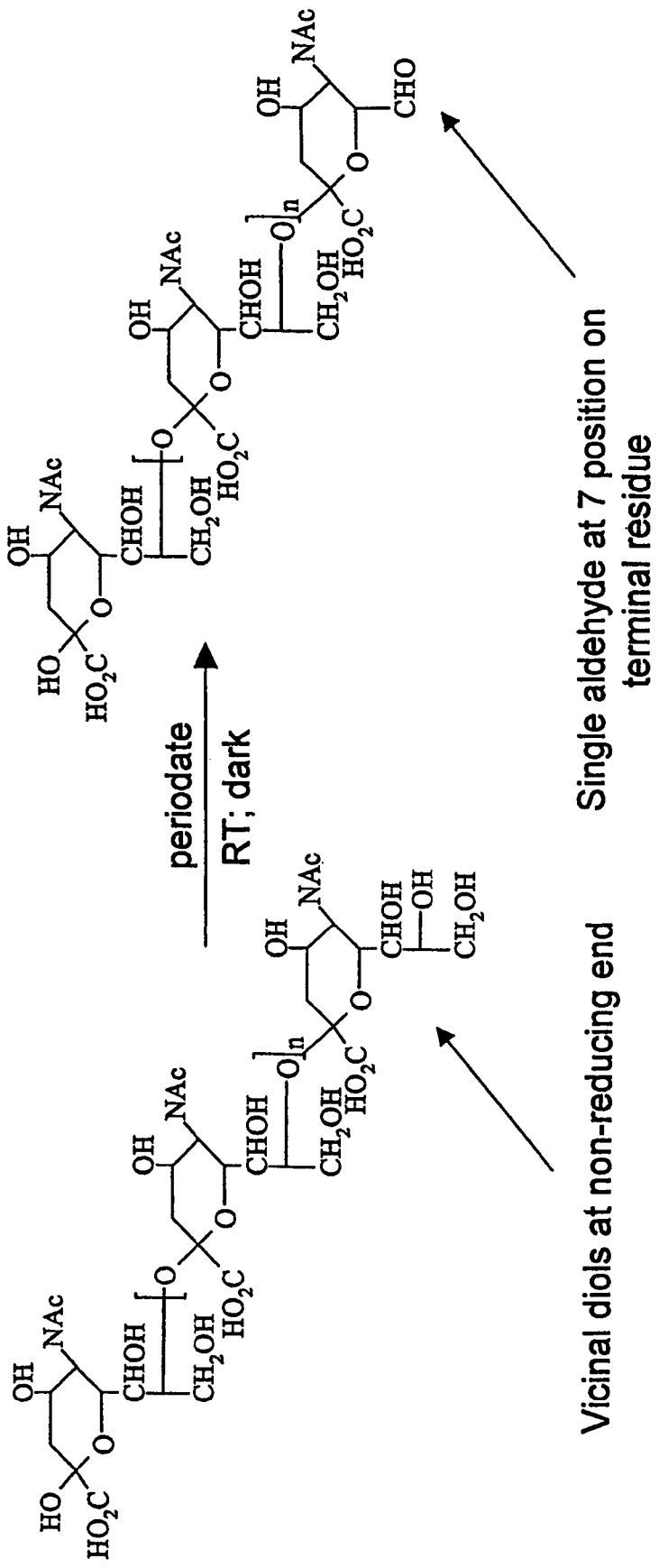
Figure 1a. Current state of the art of protein derivatisation with polysialic acid; a) oxidation of colominic acid (a form of polysialic acid) with sodium periodate to form a protein-reactive aldehyde at the non-reducing end.

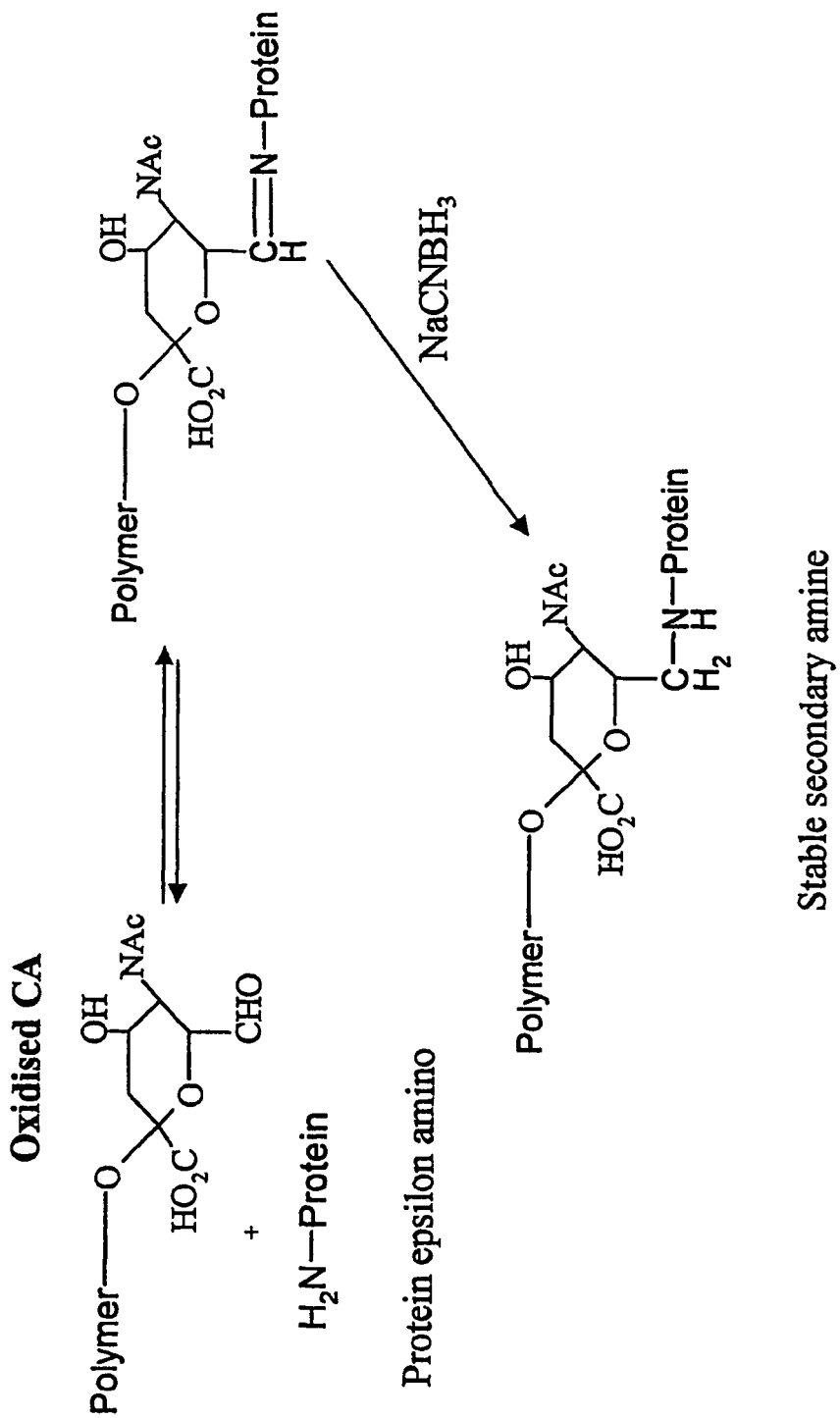
Figure 1b. Current state of the art of protein derivatisation with polysialic acid; b) selective reduction of the Schiff's base with cyanoborohydride to form a stable irreversible covalent bond with the protein amino group.

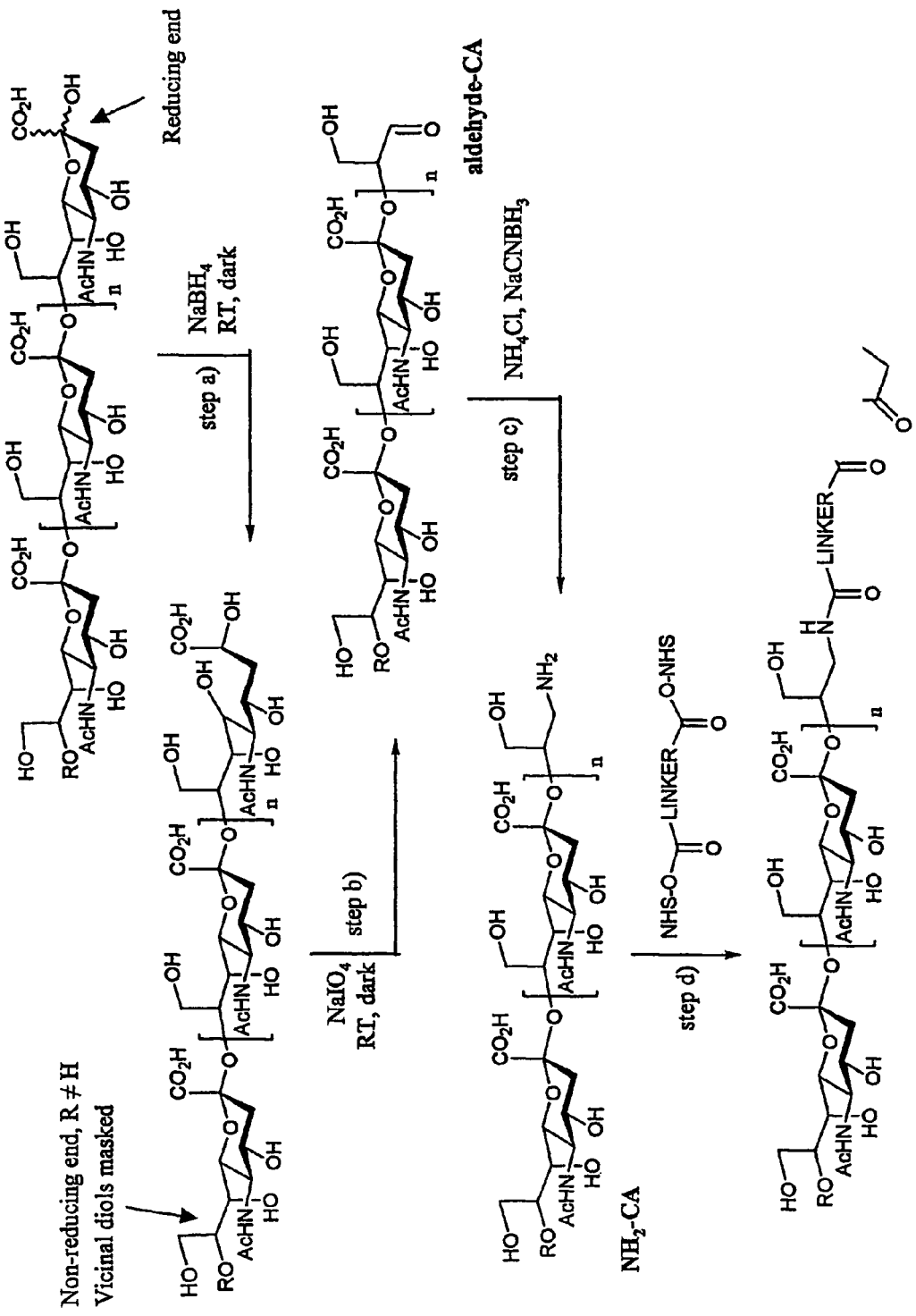
Figure 2 Preparation of reducing end derivatised NHS-CA

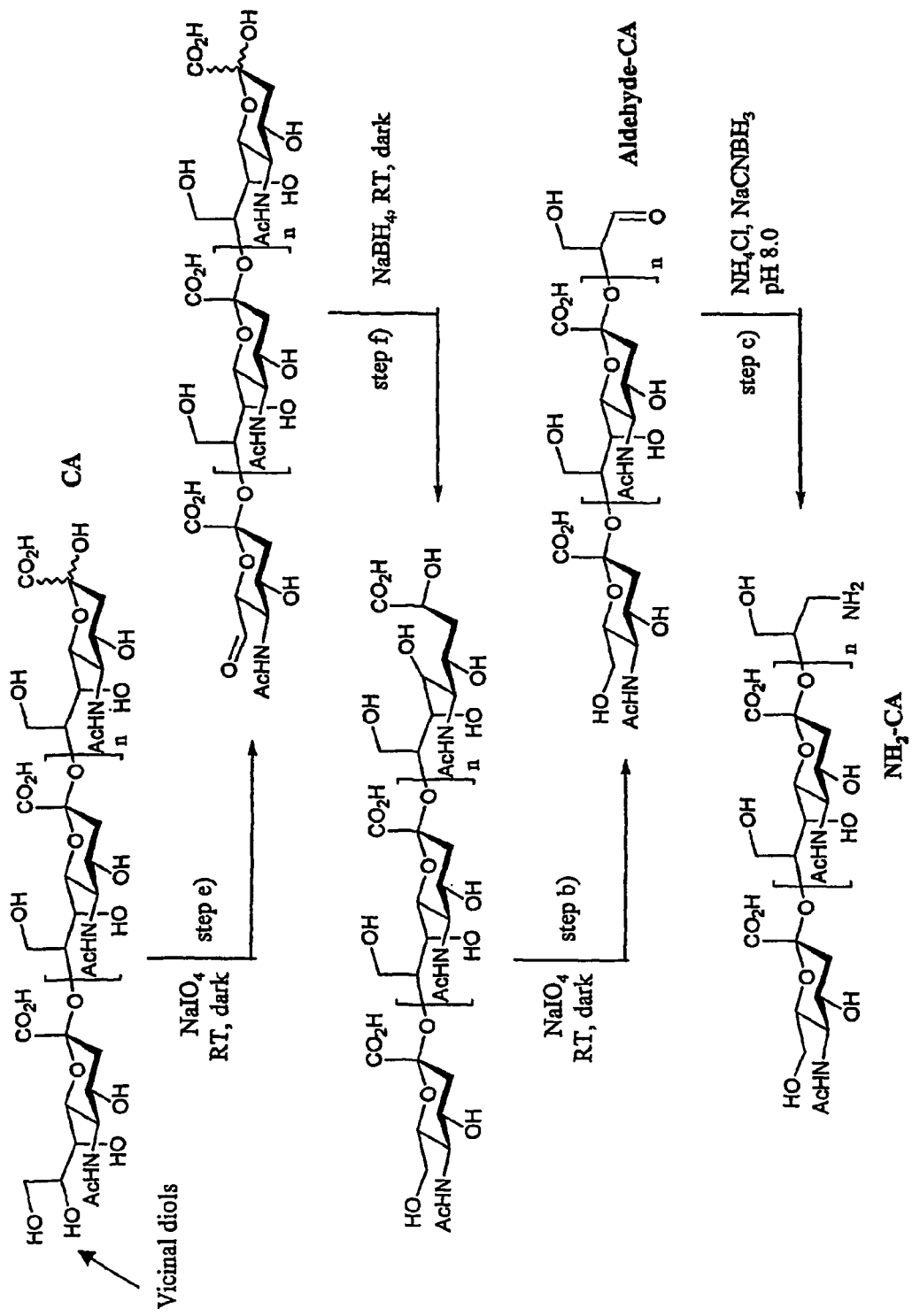
Figure 3 Preparation of reducing end derivatised CA

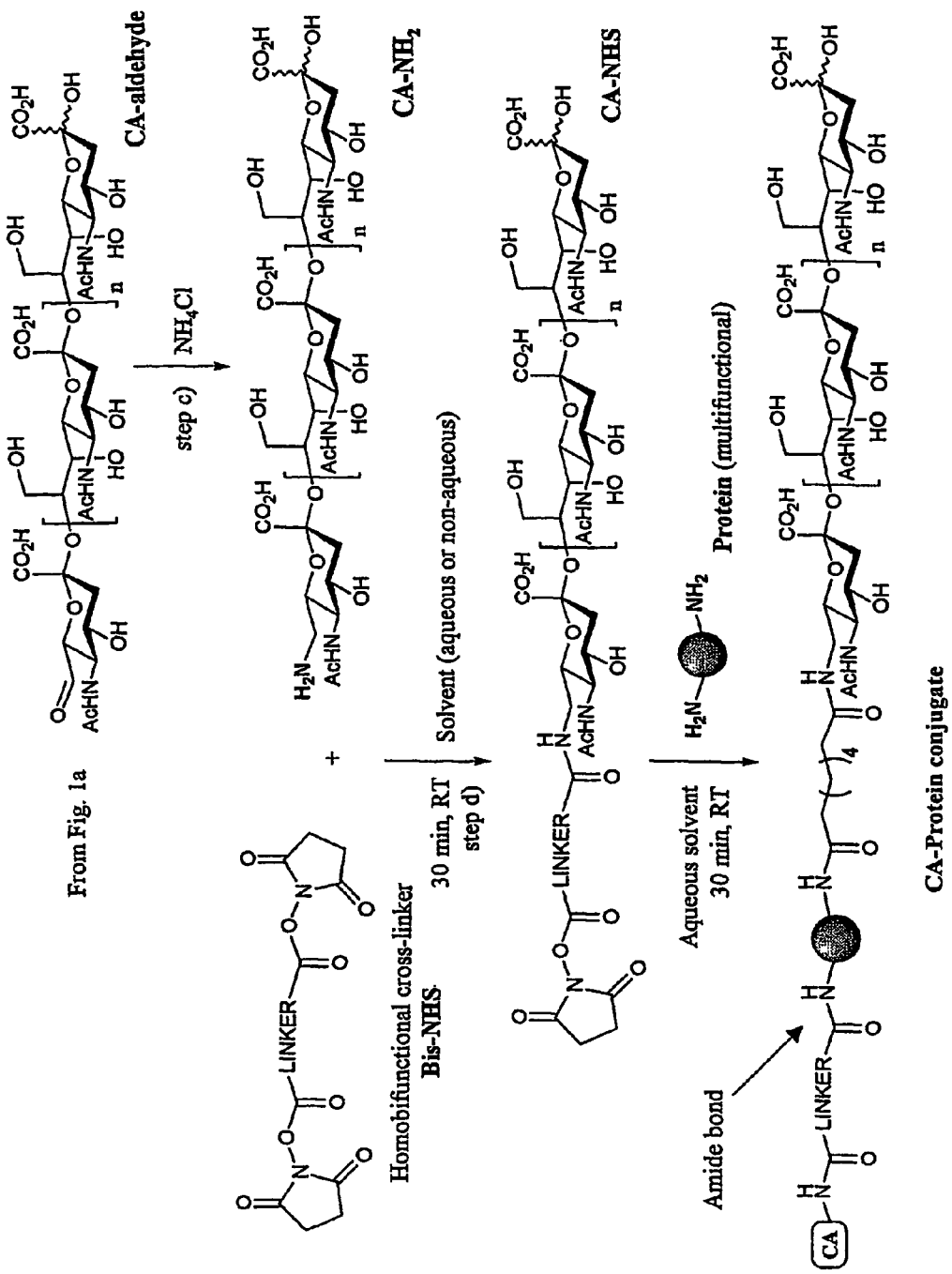
Figure 4  General Scheme for CA-protein conjugation using NHS esters

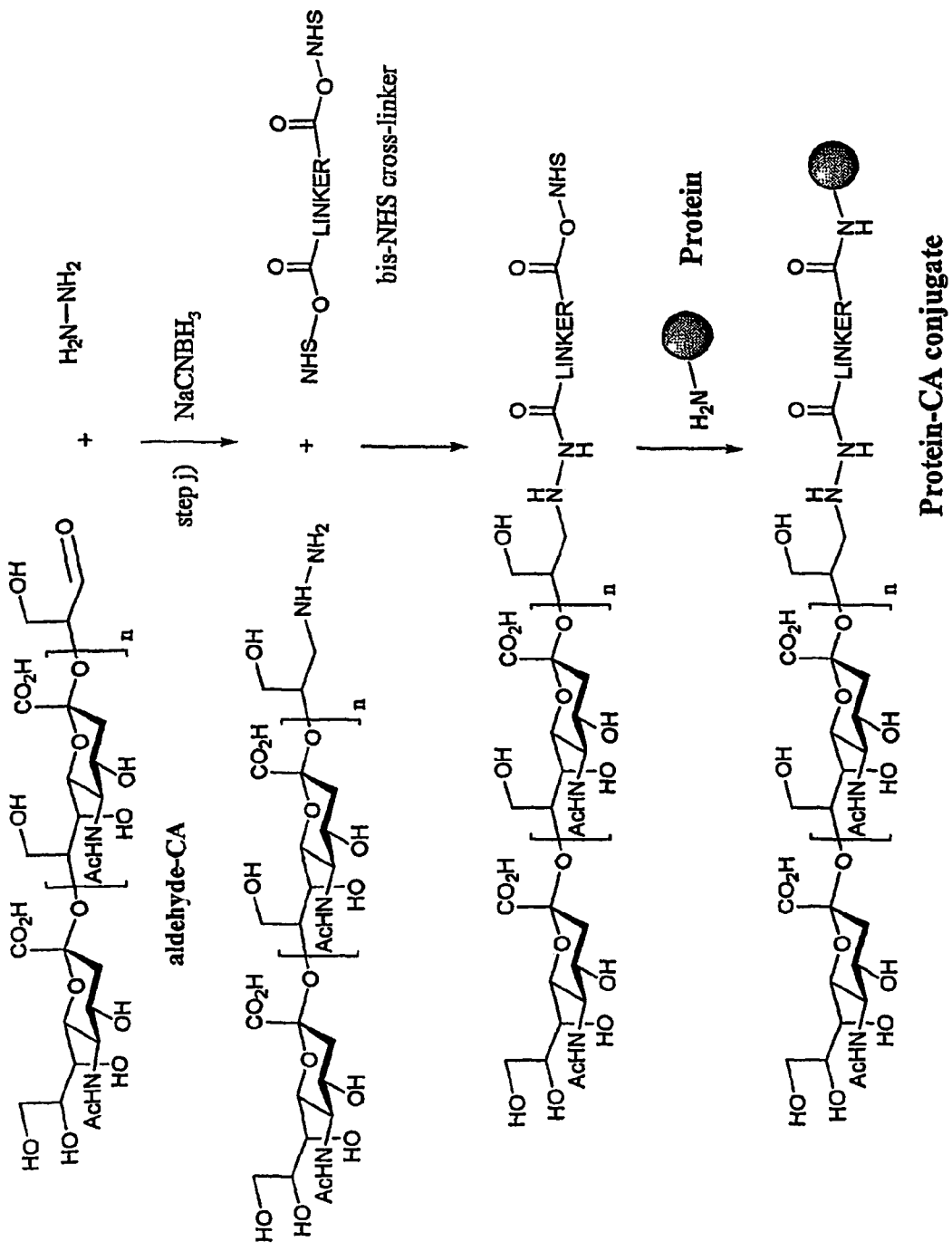
Figure 5 Preparation of CA-protein conjugates *via* NHS on reducing end

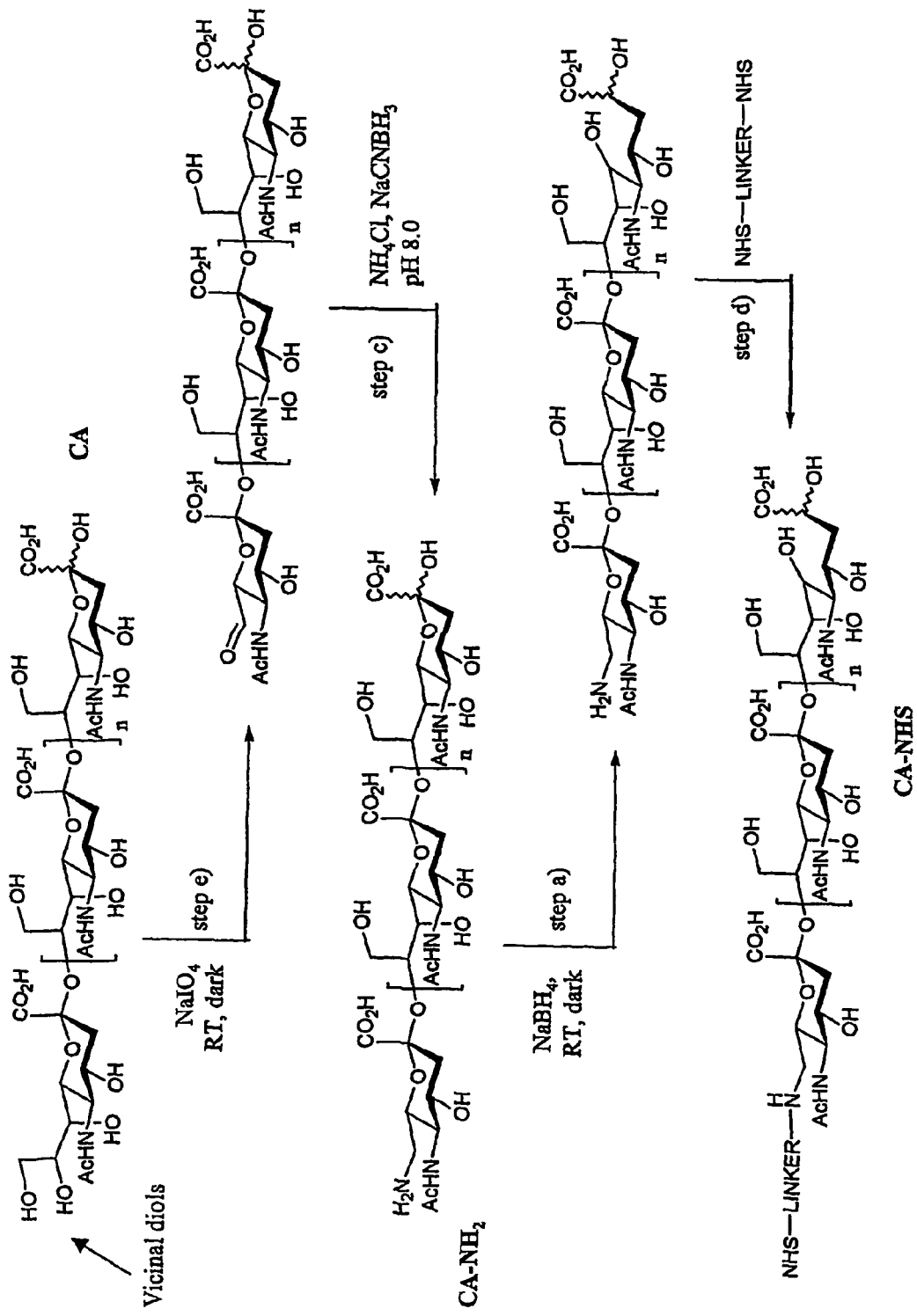
Figure 6  Preparation of non-reducing end derivatised CA

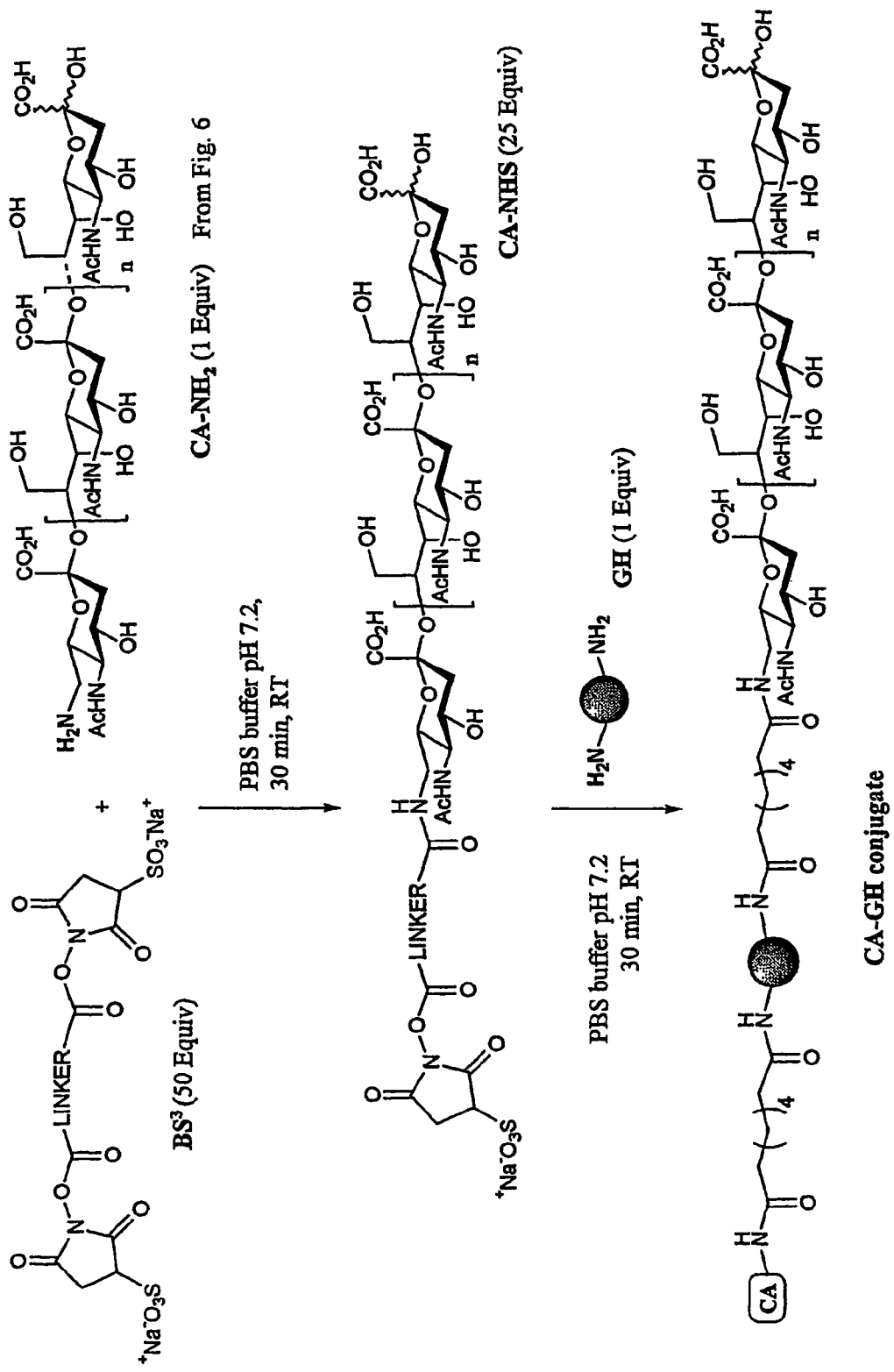
Figure 7 Preparation of CA-protein conjugates using BS³ on non-reducing end

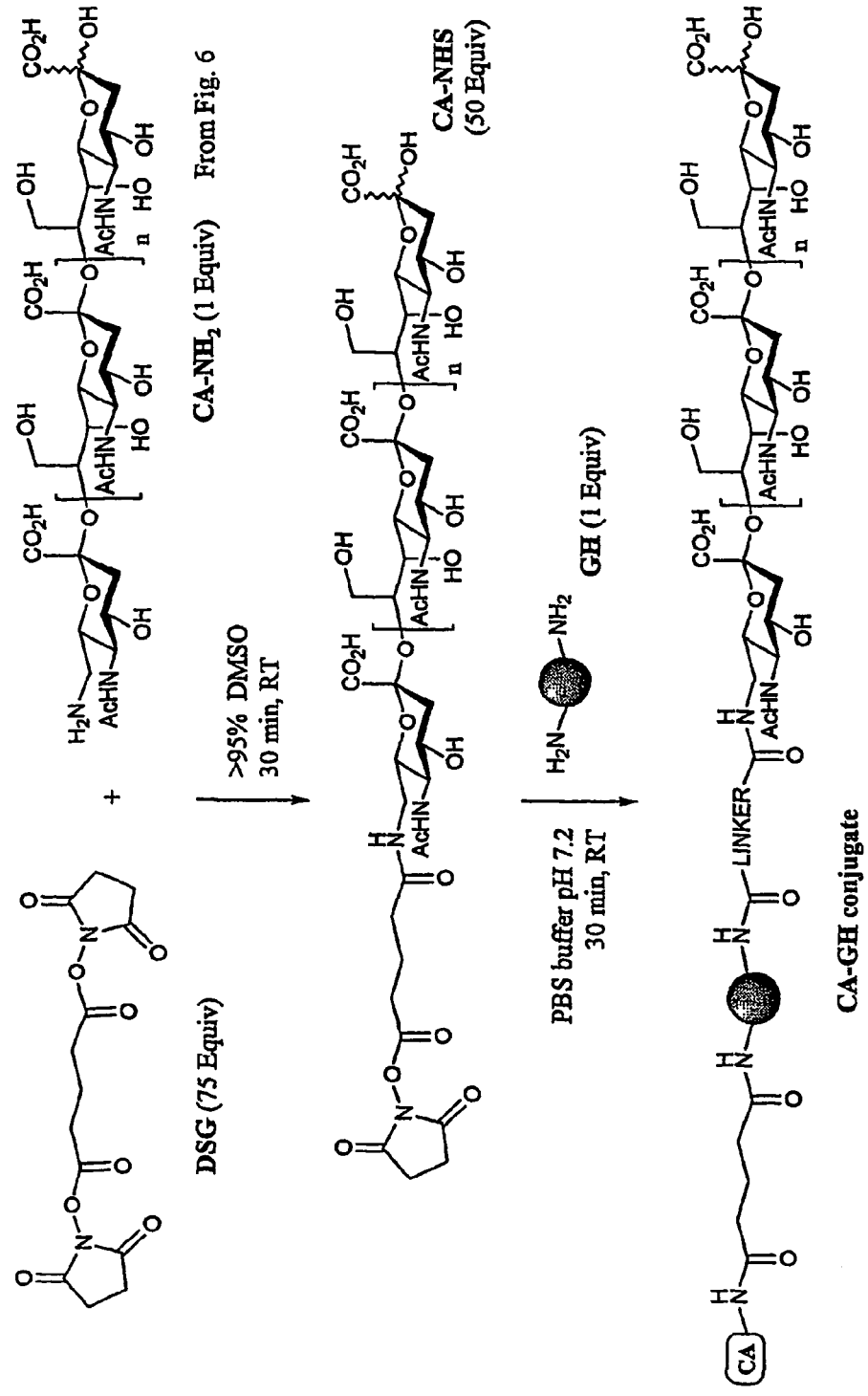
Figure 8  Preparation of CA-protein conjugates using DSG on non-reducing end

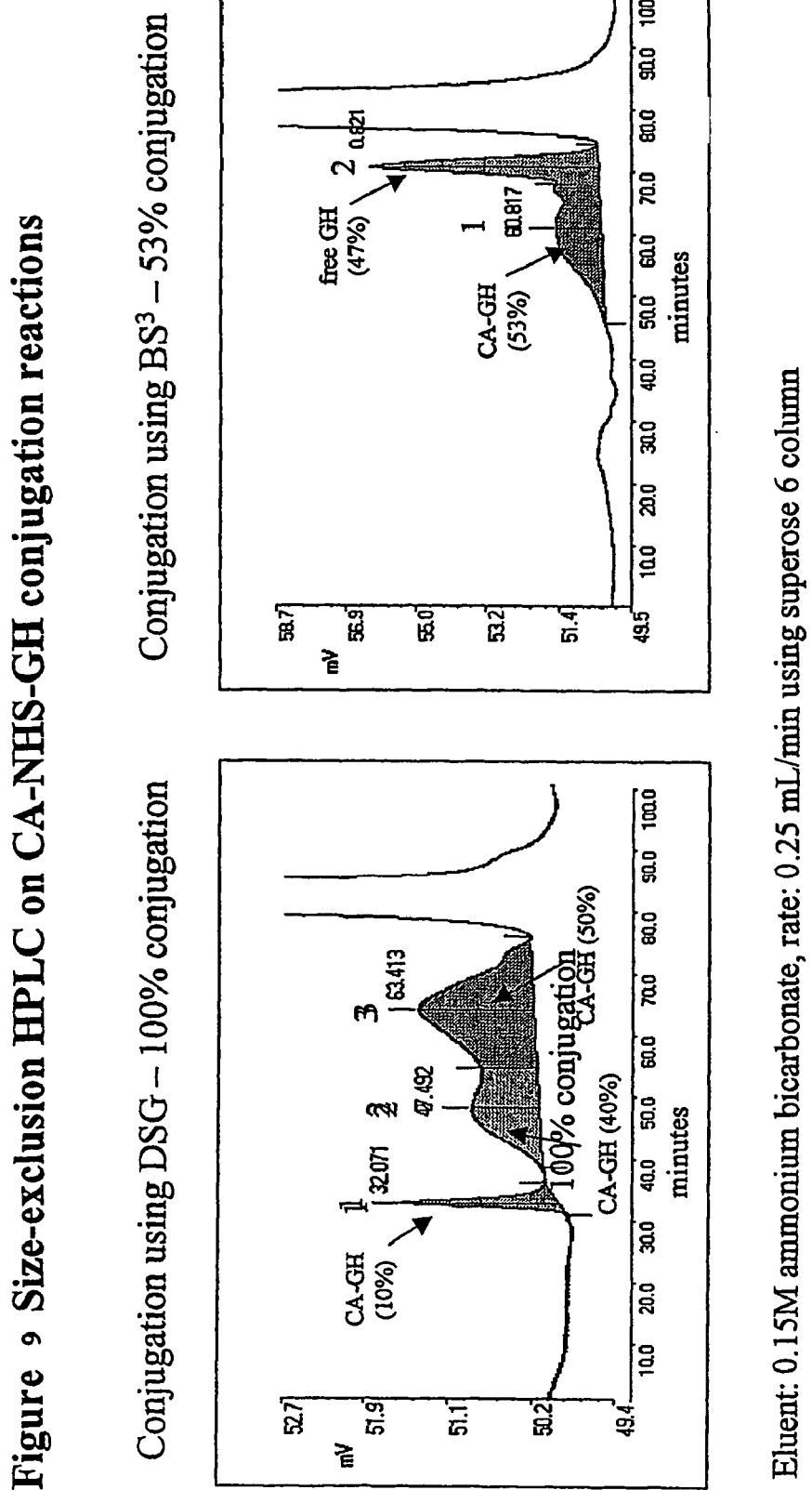
Figure 9 Size-exclusion HPLC on CA-NHS-GH conjugation reactions

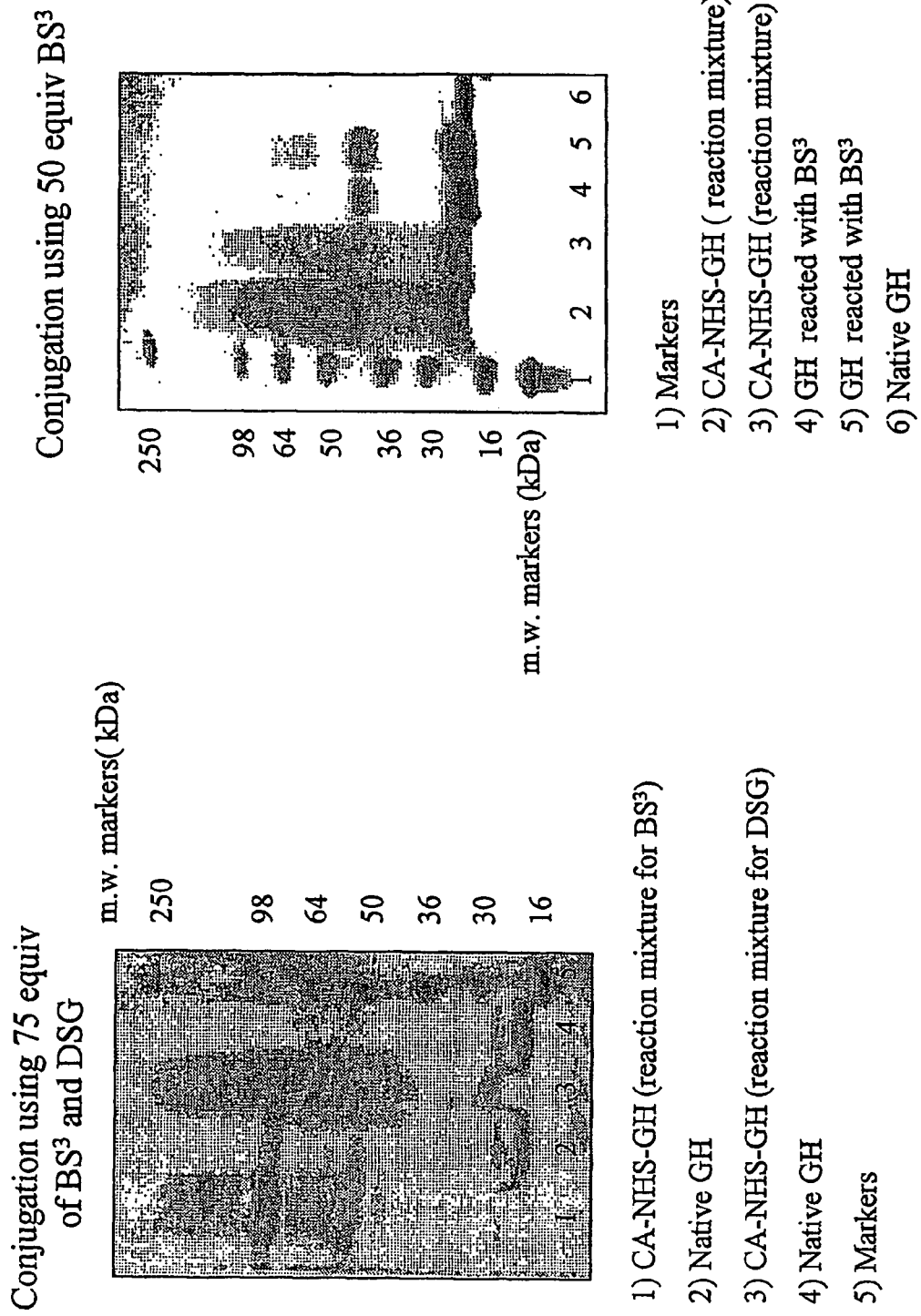
Figure 10 SDS-page of GH and GH-colominic acid conjugates

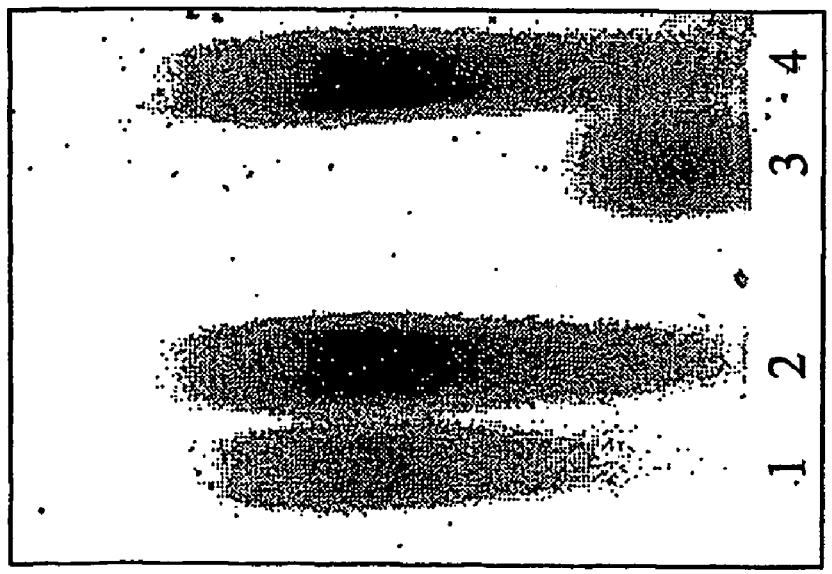
Figure 11 Native-PAGE of different CAs

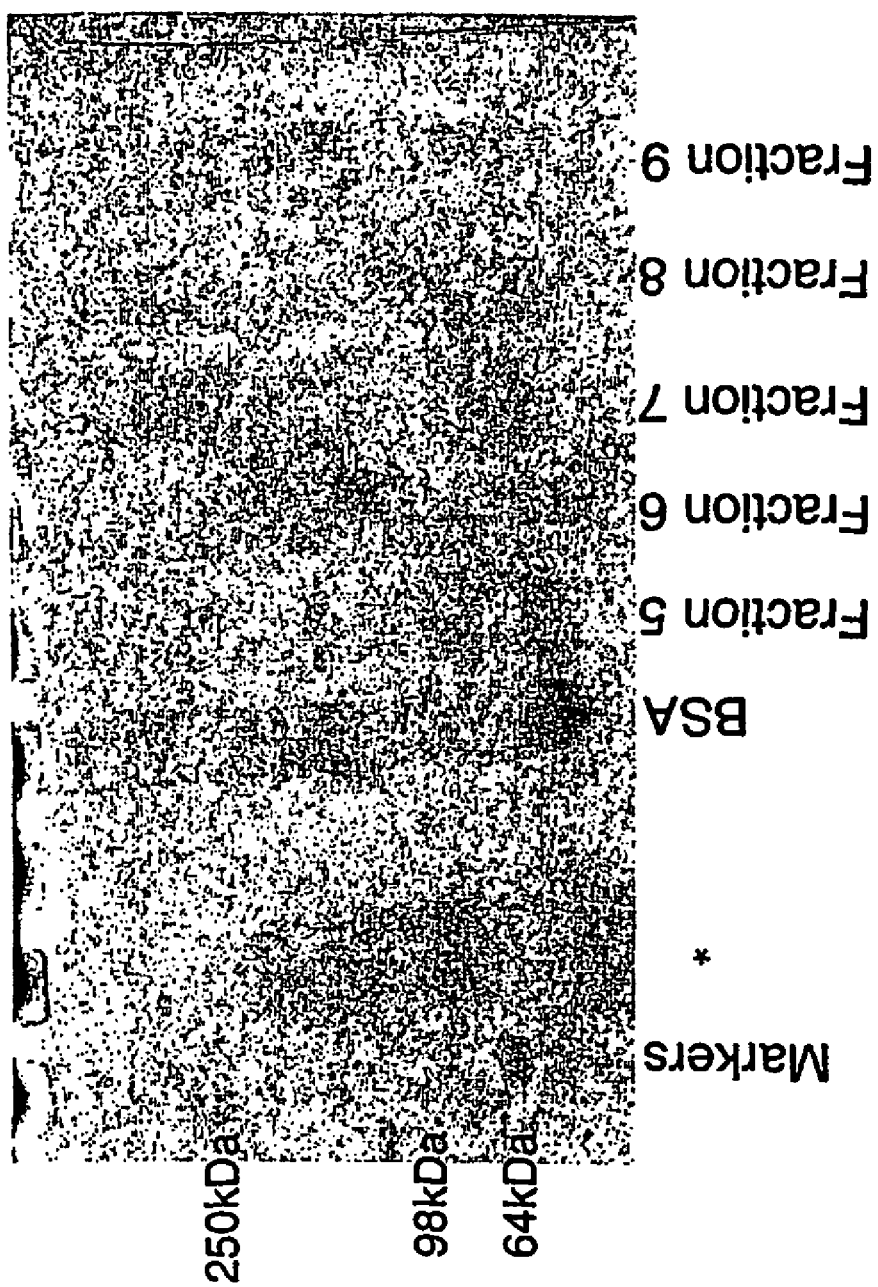
Figure 13 SDS-PAGE analysis of the CAH-NHS reactions

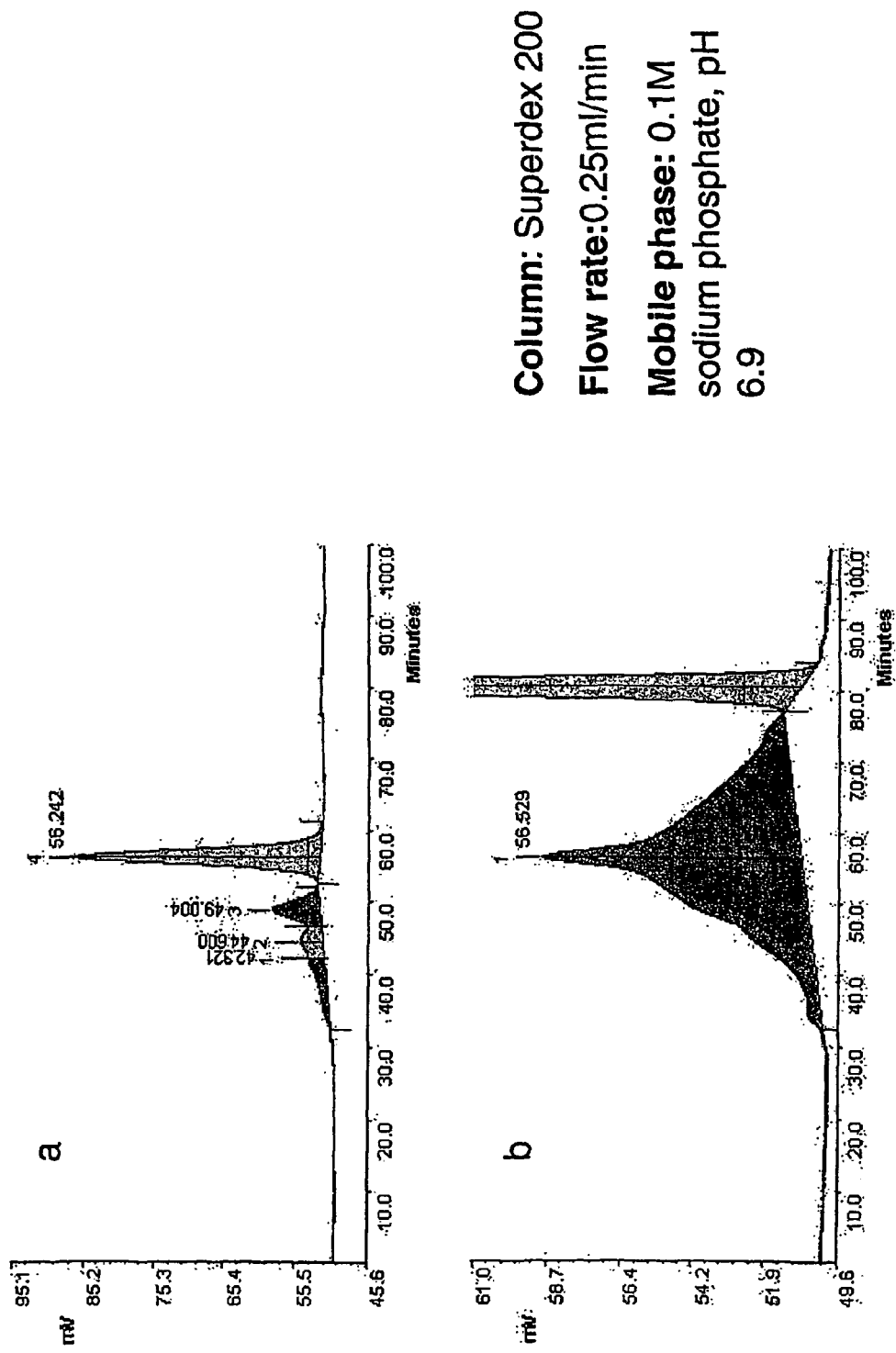
Figure 14 Size exclusion chromatography analysis

SIALIC ACID DERIVATIVES

CROSS-REFERENCE TO RELATED APPLICATIONS

This application is the national phase of PCT application PCT/GB2005/003160 having an international filing date of 12 Aug. 2005, which claims priority from European application EP 05251015.3 filed 23 Feb. 2005, and from PCT/GB04/003488 filed 12 Aug. 2004. The contents of these documents are incorporated herein by reference.

The present invention relates to derivatives of sialic acid compounds, preferably polysaccharides which have terminal or intrachain sialic acid units. Preferably the polysaccharide consists only of sialic acid units, for instance linked alpha-2, 8,2,9 to one another. The products are useful for conjugation to substrates such as peptides, proteins, drugs, drug delivery systems, viruses, cells, microbes, synthetic polymers etc. The reaction involves conjugation of an NHS group containing reagent with either an amino or hydrazide functional sialic acid derivative.

Polysialic acids (PSAs) are naturally occurring unbranched polymers of sialic acid produced in certain bacterial strains and in mammals in certain cells [Roth et. al., 1993]. They can be produced in various degrees of polymerisation: from n=about 80 or more sialic acid residues down to n=2 by either limited acid hydrolysis, digestion with neuraminidases or by fractionation of the natural, bacterial or cell derived forms of the polymer. The composition of different PSAs also varies such that there are homopolymeric forms i.e. the alpha-2,8-linked PSA comprising the capsular polysaccharide of *E. coli* strain K1 and of the group-B meningococci, which is also found on the embryonic form of the neuronal cell adhesion molecule (N-CAM). Heteropolymeric forms also exist, such as the alternating alpha-2,8 alpha-2,9 PSA of *E. coli* strain K92 and the group C polysaccharides of *N. meningitidis*. In addition, sialic acid may also be found in alternating copolymers with monomers other than sialic acid such as group W135 or group Y of *N. meningitidis*. PSAs have important biological functions including the evasion of the immune and complement systems by pathogenic bacteria and the regulation of glial adhesiveness of immature neurons during foetal development (wherein the polymer has an anti-adhesive function) [Muhlenhoff et. al., 1998; Rutishauser, 1989; Troy, 1990, 1992; Cho and Troy, 1994], although there are no known receptors for PSAs in mammals. The alpha-2, 8-linked PSA of *E. coli* strain K1 is also known as 'colominic acid' and is used (in various lengths) to exemplify the present invention.

The alpha-2,8 linked form of PSA, among bacterial polysaccharides, is uniquely non-immunogenic (eliciting neither T-cell or antibody responses in mammalian subjects) even when conjugated to immunogenic carrier protein, which may reflect its existence as a mammalian (as well as a bacterial) polymer. Shorter forms of the polymer (up to n=4) are found on cell-surface gangliosides, which are widely distributed in the body, and are believed to effectively impose and maintain immunological tolerance to PSA. In recent years, the biological properties of PSAs, particularly those of the alpha-2,8 linked homopolymeric PSA, have been exploited to modify the pharmacokinetic properties of protein and low molecular weight drug molecules [Gregoriadis, 2001; Jain et. al., 2003; U.S. Pat. No. 5,846,951; WO-A-0187922]. PSA derivatisation of a number of therapeutic proteins including catalase and asparaginase [Fernandes and Gregoriadis, 1996 and 1997] gives rise to dramatic improvements in circulation half-life, its stability and also allows such proteins to be used in the face of pre-existing antibodies raised as an undesirable (and sometimes inevitable) consequence of prior exposure to the therapeutic protein [Fernandes and Gregoriadis, 2001]. In many respects, the modified properties of polysialylated proteins are comparable to proteins derivatised with polyethylene glycol (PEG). For example, in each case, half-lives are increased, and proteins and peptides are more stable to proteolytic digestion, but retention of biological activity appears to be greater with PSA than with PEG [Hreczuk-Hirst et. al., 2002]. Also, there are questions about the use of PEG with therapeutic agents that have to be administered chronically, as PEG is only very slowly biodegradable [Beranova et. al., 2000] and both high and low molecular weight forms tend to accumulate in the tissues [Bendele, et. al., 1998; Convers, et. al., 1997]. PEGylated proteins have been found to generate anti PEG antibodies that could also influence the residence time of the conjugate in the blood circulation [Cheng et. al., 1990]. Despite the established history of PEG as a parenterally administered polymer conjugated to therapeutics, a better understanding of its immunotoxicology, pharmacology and metabolism will be required [Hunter and Moghimi, 2002; Brocchini, 2003]. Likewise there are concerns about the utility of PEG in therapeutic agents that require high dosages, (and hence ultimately high dosages of PEG), since accumulation of PEG may lead to toxicity. The alpha 2,8 linked PSA therefore offers an attractive alternative to PEG, being an immunologically 'invisible' biodegradable polymer which is naturally part of the human body, and that can degrade, via tissue neuraminidases, to sialic acid, a non-toxic saccharide.

Our group has described, in previous scientific papers and in granted patents, the utility of natural PSAs in improving the pharmacokinetic properties of protein therapeutics [Gregoriadis, 2001; Fernandes and Gregoriadis, 1996, 1997, 2001; Gregoriadis et. al., 1993, 1998, 2000; Hreczuk-Hirst et. al., 2002; Mital, 2004; Jain et. al., 2003, 2004; U.S. Pat. No. 05,846,951; WO-A-0187922]. Now, we describe new derivatives of PSAs, which allow new compositions and methods of production of PSA-derivatised proteins (and other forms of therapeutic agents). These new materials and methods are particularly suitable for the production of PSA-derivatised therapeutic agents intended for use in humans and animals, where the chemical and molecular definition of drug entities is of major importance because of the safety requirements of medical ethics and of the regulatory authorities (e.g. FDA, EMEA).

Methods have been described previously for the attachment of polysaccharides to therapeutic agents such as proteins [Jennings and Lugowski, 1981; U.S. Pat. No. 5,846,951; WO-A-01879221]. Some of these methods depend upon chemical derivatisation of the 'non-reducing' end of the polymer to create a protein-reactive aldehyde moiety (FIG. 1). The reducing end of PSA (and other polysaccharides) is only weakly reactive with proteins under the mild conditions necessary to preserve protein conformation and the chemical integrity of PSA during conjugation. The sialic acid unit, at the non-reducing terminal of PSA which contains a vicinal diol, can be readily (and selectively) oxidised with periodate to yield a mono-aldehyde derivative. This derivative is much more reactive towards proteins and comprises of a suitably reactive element for the attachment of proteins via reductive amination and other chemistries. We have described this previously in U.S. Pat. No. 5,846,951 and WO-A-0187922. The reaction is illustrated in FIG. 1 in which:

a) shows the oxidation of CA (alpha-2,8 linked PSA from *E. coli*) with sodium periodate to form a protein-reactive aldehyde at the non-reducing end of the terminal sialic acid and b) shows the reaction of the aldehyde with a primary amine group of a protein followed by the selective reduction of the Schiff's base with sodium cyanoborohydride (NaCNBH$_3$) to form a stable irreversible covalent bond with the protein amino group.

In PCT/GB04/03488 we describe polysaccharide derivatives which have a sulfhydryl-reactive group introduced via a terminal sialic acid unit. This unit is usually introduced by derivatisation of a sialic acid unit at the non-reducing end of the polysaccharide. The sulfhydryl reactive group is preferably a maleimido group. The reaction to introduce this group may involve the reaction of a heterobifunctional reagent having a sulfhydryl-reactive group at one end and a group such as a hydrazide or an ester at the other end, with an aldehyde or amine group on the sialic acid derived terminal unit of the polysaccharide. The product is useful for site specific derivatisation of proteins, e.g. at Cys units or introduced sulfhydryl groups.

Although the various methods that have been described to attach PSAs to therapeutic agents [U.S. Pat. No. 5,846,951; WO-A-01879221], are theoretically useful, achievement of acceptable yields of conjugate via reaction of proteins with the non-reducing end (aldehyde form) of the PSA requires reaction times that are not conducive to protein stability at higher temperature (e.g. interferon alpha-2b). Secondly, reactant concentrations (i.e. polymer excess) are required that may be unattainable or uneconomical.

In the invention there is provided a new process for forming derivatives of a sialic acid compound in which a starting compound comprising a terminal sialic acid unit is subjected to a preliminary intermediate—forming step, in which a group selected from a primary amine group, a secondary amine group and a hydrazine is formed on the terminal sialic acid unit, followed by a reaction step in which the intermediate is reacted with a bifunctional reagent

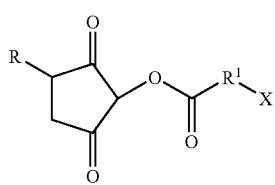

I in which R is H or sulphonyl;

$R^1$ is a linker group; and

X is a functional group, whereby the ester group is cleaved and the amine or hydrazine group of the intermediate is acylated by —CO—$R^1$—X to form the derivative.

In a first embodiment the starting compound has a terminal sialic acid unit joined to another moiety via its 2-carbon atom i.e. as a non-reducing terminal unit, and in which the preliminary step involves oxidation of the C-7, C-8 diol group of the sialic acid to form an aldehyde group followed by reductive amination with H$_2$NR$^4$, in which R$^4$ is H or lower alkyl, or acid addition salt thereof to form the intermediate. This preliminary step is shown in FIG. 3.

In this first embodiment the starting compound has the following formula:

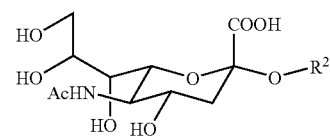

II in which R$^2$ is the said other moiety and is selected from a mono-, di-, oligo- or poly-saccharide group, a protein or peptide, a lipid, a drug and a drug delivery system (such as a liposome) and in which the amide derivative product has the following formula:

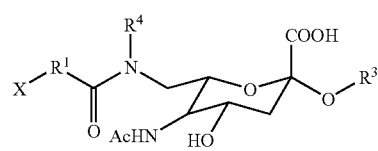

III in which X, R$^1$ and R$^4$ are the same groups as in the respective starting compounds and R$^3$ is the same as R$^2$ or is the product of the reaction thereof in the steps of oxidation, reductive amination and reaction with reagent I. The formation of a compound according to this embodiment is shown in FIG. 6, wherein the reagent I is a bis-NHS crosslinker.

In a second embodiment the starting compound has a reducing terminal sialic acid, joined to another moiety via its 8-carbon atom, and in which the preliminary step involves a ketal ring-opening reduction step whereby a group having vicinal diols is formed followed by a selective oxidation step in which the vicinal diol group is oxidised to an aldehyde group, followed by reductive amination with H$_2$NR$^4$ or acid addition salt to form the intermediate.

In this embodiment the starting compound has the following formula

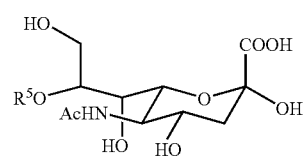

IV in which R$^5$ is the said other moiety and is selected from a saccharide group an oligo- or poly-saccharide group, an alkyl group, an acyl group, a lipid, a drug delivery system, and in which the amide product has the following formula:

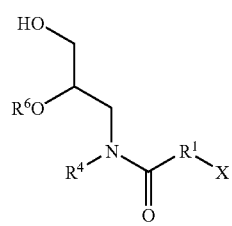

V in which $R^1$, X and $R^4$ are the same groups as in the respective starting compounds and $R^6$ is the same as $R^5$ or is the product of the reaction thereof in the steps of reduction, oxidation, amination and reaction with reagent I. The formation of a compound of formula V is shown in FIG. 2.

In a third embodiment the starting compound has a terminal sialic acid unit joined to another moiety via its 2-carbon atom (i.e. as a non-reducing terminal unit), and in which the preliminary step involves oxidation of the C-7, C-8-diol group of the sialic acid to form an aldehyde group followed by reaction with hydrazine and reduction to form the intermediate.

In this embodiment in which the starting compound has the following formula:

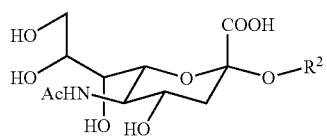

II in which $R^2$ is the said other moiety and is selected from a mono-, di-, oligo- or poly-saccharide group, a protein or peptide, a lipid, a drug or a drug delivery system and in which the product derivative has the following formula

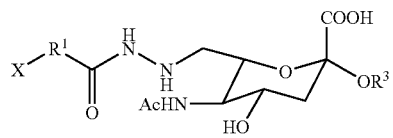

VIII in which X and $R^1$ are the same as in the respective starting materials and $R^3$ is the same as $R^2$ or is the product of the reaction thereof in the steps of oxidation, reaction with hydrazine, reduction and reaction with reagent I.

In a fourth embodiment the starting compound has a reducing end terminal sialic acid, joined to another moiety via its 8-carbon atom, and in which the preliminary step involves a ketal ring-opening reduction step whereby a group having vicinal diols is formed followed by a selective oxidation step in which the vicinal diol group is oxidised to an aldehyde group, followed by reaction with hydrazine and reduction to form the intermediate.

In this embodiment in which the starting compound has the following formula

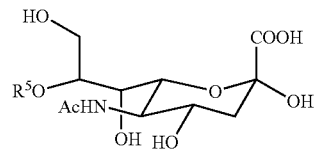

IV in which $R^5$ is the said other moiety and is selected from a mono-, di-, oligo- and poly-saccharide group, an alkyl group, an acyl group, a lipid and a drug delivery system, and in which the product derivative has the following formula

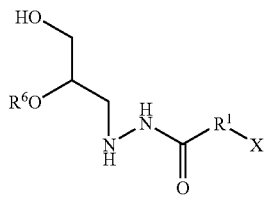

IX in which X, $R^1$ are same groups as in the respective starting compounds and in which $R^6$ is the same as $R^5$ or is the product of the reaction thereof in the steps of reduction, oxidation, reaction with hydrazine, reduction and reaction with reagent I. An example of a reaction scheme which produces compounds of formula IX is shown in FIG. 5, wherein the bifunctional reagent I is bis-NHS.

In the process it is generally important that the intermediate is isolated substantially from the product mixture of the preliminary step prior to being contacted with the reagent of formula I. This is because the reagents used in the preliminary step(s) may inactivate the reagent of formula I. In addition, where the preliminary step involves sequential steps of oxidation and reduction or vice versa the oxidising agents or reducing agents of the first step should be inactivated before adding the reagent for the subsequent step.

In the process of the invention, it is convenient for the reaction between the intermediate and the reagent of formula I to be conducted in an aprotic solvent, preferably comprising a small amount of a protic solvent. Minimising the level of protic solvent present in the reaction avoids premature deactivation of the NHS group of the reagent of formula I. In general aprotic solvents are found to damage biological molecules. It is surprising that the use of dimethylsulphoxide DMSO, specifically to solubilise PSAs, results in good levels of conjugation to NHS reagents, without excess levels of deactivation of the NHS groups prior to reaction, and allows recovery of the derivative from the product mixture. Preferably therefore the aprotic solvent is DMSO.

The reagent of formula I is generally used in an amount which is in stoichiometric excess for reaction with the intermediate, and is preferably present in an amount at least twice, more preferably at least five times the amount for stoichiometric reaction with the intermediate.

In one embodiment of the reagent of formula I, X is a group

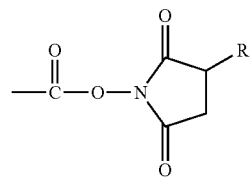

in which R has the same definition as above.

In an alternative embodiment X is a group selected from the group consisting of vinylsulphone, N-maleimido, N-iodoacetamido, orthopyridyl disulfide, protected hydroxyl, protected amino, and azido.

The reagent of formula I is preferably selected from:
N-(α-maleimidoacetoxy)succinimide ester, (AMAS),
N-(β-maleimidopropyloxy)succinimide ester, (BMPS), N-(ξ-maleimidocapryloxy)succinimide ester, (EMCS), or its sulfo analog, N-(γ-maleimidobutyryloxy)succinimide ester, (GMBS), or its sulfo analog, succinimidyl-4-(N-maleimidomethyl)-cyclohexane-1-carboxy-6-amidocaproate), (LC-SMCC), m-maleimido benzoyl-N-hydroxysuccinimide ester (MBS), or, its sulfo analog, succinimidyl-4-(N-maleimidomethyl)-cyclohexane-1-carboxyate) (SMCC) or its sulfo analog, succinimidyl-4-(p-maleimido phenyl) butyrate (SMPB) or its sulfo analog, succinimidyl-6-(β-maleimido-propionamido) hexanoate (SMPH), N-(k-maleimidoundecanoyloxy) sulfosuccinimide-ester (sulfo-KMUS), succinimidyl 6-[3-2(2-pyridyidithio)-propionamido]hexanoate (LC-SPDP) or its sulfo analog, 4-succinimidyloxycarbonyl-methyl-α-(2-pyridyidithio) toluene (SMPT) or its sulfo-LC analog, N-succinimidyl-3-(2-pyridyidithio)propionate (SPDP), N-succinimidyl [4-vinylsulfonyl) benzoate (SVSB), succinimidyl 3-(bromoacetamido)propionate (SBAP), and N-succinimidyliodoacetate (SIA) and N-succinimidyl(4-iodoacetyl)aminobenzoate (SIAB) or its sulfo analog.

Another category of heterobifunctional reagents of formula I have photoreactive groups as X, such as azide groups. Examples of such reagents are:

N-5-Azido-2-nitrobenzoyloxysuccinimide water insoluble (ANB-NOS),

N-Hydroxysuccinimidyl-4-azidosalicylic acid water insoluble, non-cleavable (NHS-ASA), N-Succinimidyl (4-azidophenyl)-1,3'-dithiopropionate (SADP), Sulfosuccinimidyl 2-(7-azido-4-methyl-coumarin-3-acetamido) ethyl-1,3'-dithiopropionate (SAED), Sulfosuccinimidyl 2-(m-azido-o-nitro-benzamido)ethyl-1,3'-dithiopropionate (SAND), N-Succinimidyl 6-(4'-azido-2'-nitro-phenylamino)hexanoate (SANPAH), Sulfosuccinimidyl 2-(p-azido-o-salicylamido)ethyl-1,3'-dithiopropionate (SASD), Sulfosuccinimidyl-(perfluoroazidobenzamido) ethyl-1,3'-dithiopropionate (SFAD), and N-Hydroxysulfosuccinimidyl-4-azidobenzoate (Sulfo-HSAB).

The reagent of formula I may be selected from bis[2-succinimidyloxycarbonyl-oxy)ethyl]sulfone (BSOCOES) and its sulfo analog, bis(sulfosuccinimidyl)suberate) (BS$^3$), disuccinimidyl glutarate (DSG), dithiobis (succinimidyl propionate) (DSP), disuccinimidyl suberate (DSS), disuccinimidyl tartrate (DST) or its sulfo analog, 3,3'-dithiobis (sulfosuccinimidyl propionate) (DTSSP), and ethylene glycol bis(succinimidyl succinate) (EGS) and its sulfo analog.

The group $R^1$ is a difunctional organic radical. Preferably, $R^1$ is selected from the group consisting of alkanediyl, arylene, alkarylene, heteroarylene and alkylheteroarylene, any of which may substituted and/or interrupted by carbonyl, ester, sulfide, ether, amide and/or amine linkages. Particularly preferred is $C_3$-$C_6$ alkanediyl. Most preferably, $R^1$ corresponds to the appropriate portion of one of the preferred reagents I listed above. The substituent group may be chosen from those listed for $R^1$ above, or alternatively may be an amino acid side chain.

In the process preferably the product derivative is isolated substantially completely from any excess reagent.

Reaction conditions for the reactions generally used may also be used here, for instance with reference to Hermanson, (1995).

More preferably, the product amide derivative is isolated substantially completely from the product mixture. Such isolation and recovery may involve a drying step preferably carried out under reduced pressure and most preferably a freeze-drying step.

Thus reactive sialic acid derivatives useful for subsequent reaction with biologically useful compounds may be made available in a stable form.

The invention is illustrated further in the accompanying examples and Figures.

The following is a brief description of the drawings:

FIG. 1a is a reaction scheme showing the prior art activation of the non-reducing sialic acid terminal unit;

FIG. 1b is a reaction scheme showing the prior art reductive amination of the aldehyde moiety of reaction scheme 1a using a protein-amine moiety;

FIG. 2 shows the preparation of reducing and derivatised NHS colominic acid (when non-reducing end has no vicinal diol);

FIG. 3 shows the preparation of reducing end derivatised $NH_2$-CA colominic acid (vicinal diol removed at non-reducing end);

FIG. 4 shows the general scheme for preparation of CA-NHS-protein conjugation;

FIG. 5 shows the preparation of CA-protein conjugates via NHS on reducing end;

FIG. 6 shows preparation of non-reducing end derivatised CA;

FIG. 7 shows the preparation of CA-protein conjugates using bis(sulfosuccinimidyl) suberate (BS$^3$) on non-reducing end;

FIG. 8 shows the schematic reprsentation of CA-protein conjugation using the crosslinker DSG;

FIG. 9 shows the HPLC of the CA-GH conjugation reactions;

FIG. 10 shows the sodium dodecyl sulphate (SDS)-polyacrylamide gel eletrophoresis (PAGE) of CA-NHS-GH conjugates (CA 35 kDa);

FIG. 11 shows native PAGE of unreacted CAs;

FIG. 13 shows the SDS-PAGE analysis of the CAH-NHS reactions; and

FIG. 14 shows the size exclusion chromatography analysis of the CAH-NHS reactions.

EXAMPLES

Materials

Figure 12:
FIG. 12 shows the SDS-PAGE of CAM-β-gal and CAI-β-gal conjugates.

Sodium meta-periodate and molecular weight markers were obtained from Sigma Chemical Laboratory, UK. The CAs used, linear alpha-(2,8)-linked E. coli K1 PSAs (22.7 kDa average, polydispersity (p.d.) 1.34; 39 kDa p.d. 1.4; 11 kDa, p.d. 1.27) were from Camida, Ireland. Other materials included 2,4dinitrophenyl hydrazine (Aldrich Chemical Company, UK), dialysis tubing (3.5 kDa and 10 kDa cut off limits (Medicell International Limited, UK); Sepharose SP HiTrap, PD-10 columns (Pharmacia, UK); XK50 column (Amersham Biosciences, UK); Sepharose Q FF (Amersham Biosciences); Tris-glycine polyacrylamide gels (4-20% and 16%), Tris-glycine sodium dodecylsulphate running buffer and loading buffer (Novex, UK). Deionised water was obtained from an Elgastat Option 4 water purification unit (Elga Limited, UK). All reagents used were of analytical grade. A plate reader (Dynex Technologies, UK) was used for spectrophotometric determinations in protein or CA assays.

Methods

Protein and CA Determination

Quantitative estimation of CAs, as sialic acid, was carried out by the resorcinol method [Svennerholm 1957] as described elsewhere [Gregoriadis et. al., 1993; Fernandes and Gregoriadis, 1996, 1997]. GH was measured by the bicinchoninic acid (BCA) calorimetric method.

Reference Example 1

Fractionation of CA by IEC (CA, 22.7 kDa, pd 1.34)

An XK50 column was packed with 900 ml Sepharose Q FF and equilibrated with 3 column volumes of wash buffer (20 mM triethanolamine; pH 7.4) at a flow rate of 50 ml/min. CA (25 grams in 200 ml wash buffer) was loaded on column at 50 ml/min via a syringe port. This was followed by washing the column with 1.5 column volumes (1350 ml) of washing buffer.

The bound CA was eluted with 1.5 column volumes of different elution buffers (Triethanolamine buffer, 20 mM pH 7.4, with 0 mM to 475 mM NaCl in 25 mM NaCl steps) and finally with 1000 mM NaCl in the same buffer to remove all residual CA and other residues (if any).

The samples were concentrated to 20 ml by high pressure ultra filtration over a 5 kDa membrane (Vivascience, UK). These samples were buffer exchanged into deionised water by repeated ultra filtration at 4° C. The samples were analysed for average molecular weight and other parameters by GP) and native PAGE (stained with alcian blue). Narrow fractions of CA produced using above procedure were oxidised with sodium periodate and analysed by GPC and native PAGE for gross alteration to the polymer.

Reference Example 2

Activation of CA

Freshly prepared 0.02 M sodium metaperiodate ($NaIO_4$; 6 fold molar excess over CA) solution was mixed with CA at 20° C. and the reaction mixture was stirred magnetically for 15 min in the dark (as shown in the first step of FIG. 3). The oxidised CA was precipitated with 70% (final concentration) ethanol and by centrifuging the mixture at 3000 g for 20 minutes. The supernatant was removed and the pellet was dissolved in a minimum quantity of deionised water. The CA was again precipitated with 70% ethanol and then centrifuged at 12,000 g. The pellet was dissolved in a minimum quantity of water, lyophilized and stored at −20° C. until further use.

Reference Example 3

Determination of the Oxidation State of CA and Derivatives

Quantitative estimation of the degree of CA oxidation was carried out with 2,4 dinitrophenylhydrazine (2,4-DNPH), which yields sparingly soluble 2,4 dinitrophenyl-hydrazones on interaction with carbonyl compounds. Non-oxidised (CA) and oxidised CA (CAO) (5 mg each) were added to the 2,4-DNPH reagent (1.0 ml), the solutions were shaken and then allowed to stand at 37° C. until a crystalline precipitate was observed [Shriner et. al., 1980]. The degree (quantitative) of CA oxidation was measured with a method [Park and Johnson, 1949] based on the reduction of ferricyanide ions in alkaline solution to ferric ferrocyanide (Persian blue), which is then measured at 630 nm. In this instance, glucose was used as a standard.

Reference Example 4a

Preparation of Amino Colominic Acid ($CA-NH_2$)

CAO produced as in Reference Example 2 at 10-100 mg/ml was dissolved in 2 ml of deionised water with a 300-fold molar excess of $NH_4Cl$, in a 50 ml tube and then $NaCNBH_4$ (5 M stock in 1 N NaOH(aq)), was added at a final concentration of 5 mg/ml (FIG. 4, first step). The mixture was incubated at room temperature for 5 days. A control reaction was also set up with CA instead of CAO. Product colominic acid amine derivative was precipitated by the addition of 5 ml ice-cold ethanol. The precipitate was recovered by centrifugation at 4000 rpm, 30 minutes, room temperature in a benchtop centrifuge. The pellet was retained and resuspended in 2 ml of deionised water, then precipitated again with 5 ml of ice-cold ethanol in a 10 ml ultracentrifuge tube. The precipitate was collected by centrifugation at 30,000 rpm for 30 minutes at room temperature. The pellet was again resuspended in 2 ml of deionised water and freeze-dried.

Reference Example 4b

Assay for Amine Content

The TNBS (picrylsulphonic acid, i.e. 2,4,6-tri-nitro-benzene sulphonic acid) assay was used to determine the amount of amino groups present in the product [Satake et. al., 1960].

In the well of a microtitre plate TNBS (0.5 µl of 15 mM TNBS) was added to 90 µl of 0.1 M borate buffer pH 9.5. To this was added 10 µl of a 50 mg/ml solution of CA-amide the plate was allowed to stand for 20 minutes at room temperature, before reading the absorbance at 405 nm. Glycine was used as a standard, at a concentration range of 0.1 to 1 mM. TNBS trinitrophenylates primary amine groups. The TNP adduct of the amine is detected.

Testing the product purified with a double cold-ethanol precipitation using the TNBS assay showed close to 90% conversion.

Example 1

Preparation of CA-NHS $CA-NH_2$ (35 kDa) (15-20 mg) synthesised in Reference Example 4a above was dissolved in 0.15M PBS (350 µL, pH 7.2) and then either 50 or 75 molar equivalents of $BS^3$ in PBS (150 µL, PH 7.2) was added. The mixture was vortexed for 5 seconds and then reacted for 30 minutes at 20° C. This is shown generally in FIG. 4, second step, for a homobifunctional cross-linker and more specifically in FIG. 7 for $BS^3$. The CA-NHS product was purified by PD-10 column using PBS as eluent (pH 7.2) and used immediately for site-specific conjugation to the $NH_2$ groups in proteins and peptides. Determination of the CA concentration from the PD 10 fractions was achieved by analysing the sialic acid content using the resorcinol assay. The NHS content on the CA polymer was measured by UV spectroscopy by analysing the CA and NHS reaction solution at 260 nm and also by thin layer chromatography with visualization at 254 nm.

CA-NH$_2$ (35 kDa) (15-20 mg) synthesised in Example 1 above was either dissolved in the minimum amount of water (50-65 µL) to which was added DMSO (300-285 µL) or in >95% DMSO (350 µL) with the aid of heat (100-125° C.). 75 molar equivalents of DSG in DMSO (150 L) was added to the CA-NH$_2$ solution, vortexed for 5 seconds and then reacted for 30 minutes at 20° C. (FIG. 8). The CA-NHS product was purified either with dioxane precipitation (×2) or by PD-10 column using PBS as eluent (pH 7.2) and used immediately for site-specific conjugation to the NH$_2$ groups in proteins and peptides. As before determination of the CA concentration from the PD-10 fractions was measured using the resorcinol assay. The NHS content on the CA polymer was measured by UV spectroscopy (260 nm) and by thin layer chromatography (254 nm).

Example 2

Preparation of CA-NHS-Protein Conjugates (using BS$^3$ and DSG)

GH in sodium bicarbonate (pH 7.4) was covalently linked to CA-NHS (35 kDa), from reference example 4b with an excess of BS$^3$. The reaction was performed in 0.15 M PBS (pH 7.2; 1.5 ml) using a molar ratio of 25:1 or 50:1 of CA-NHS:GH for a period of 30 minutes at 20° C. Polysialylated GH was characterised by SDS-PAGE and the conjugation yield determined by FPLC-size exclusion chromatography. Controls included subjecting the native protein to the conjugation procedure using BS$^3$ in the absence of any CA-NHS. CA-NH$_2$ was also subjected to the conjugation procedure using BS$^3$ in the absence of native GH.

GH in sodium bicarbonate (pH 7.4) was covalently linked to CA-NHS (35 kDa), which was prepared as discussed in example 4b using an excess of DSG. The reaction was performed in 0.15 M PBS (pH 7.2; 1.5 ml) using a molar ratio of 50:1 of CA-NHS:GH for a period of 30 minutes at 20° C. Polysialylated GH was characterised by SDS-PAGE and the conjugation yield determined by HPLC-size exclusion chromatography. Controls included subjecting the native protein to the conjugation procedure using DSG in the absence of any CA-NHS.

CA-GH conjugates were dissolved in ammonium bicarbonate buffer (0.2M; pH7) and were chromatographed on superose 6 column with detection by UV index (Agilent, 10/50 system, UK). Samples (1 mg/ml) were filtered over 0.45 µm nylon membrane 175 µl injected and run at 0.25 cm/min with ammonium bicarbonate buffer as the mobile phase. (FIG. 9).

SDS-PAGE (MiniGel, Vertical Gel Unit, model VGT 1, power supply model Consort E132; VWR, UK) was employed to detect changes in the molecular size of GH upon polysialylation. SDS-PAGE of GH and its conjugates (with CA-NHS) of 0 (control) and 30 minutes samples from the reaction mixtures as well as a process control (non oxidised CA), was carried out using a 4-20% polyacrylamide gel. The samples were calibrated against a wide range of molecular weight markers (FIGS. 10 and 11).

Results

CA and its derivatives (22.7 kDa) were successfully fractionated into various narrow species with a polydispersity less than 1.1 with m.w. averages of up to 46 kDa with different % of populations. Table 2 shows the results of separating the 22.7 kDa material.

TABLE 2

Ion exchange chromatography of CA22.7(pd 1.3)

| Elution buffers (in 20 mM Triethanolamine buffer + mM NaCl, pH 7.4) | M.W. | Pd | % Population |
|---|---|---|---|
| 325 mM | 12586 | 1.091 | 77.4% |
| 350 mM | 20884 | 1.037 | 3.2% |
| 375 mM | 25542 | 1.014 | 5.0% |
| 400 mM | 28408 | 1.024 | 4.4% |
| 425 mM* | | | 7.4% |
| 450 mM | 43760 | 1.032 | 2.3% |
| 475 mM | 42921 | 1.096 | 0.2% |

*Not done

This process was scalable from 1 ml to 900 ml of matrix with the fractionation profile almost identical at each scale (not all results shown).

[The fractionation of larger polymer (CA, 39 kDa, pd 1.4) produced species up to 90 kDa. This process can successfully be used for the fractionation of even large batches of the polymer. The results show that the ion exchange fractions are narrowly dispersed. This is consistent with the GPC data.]

All narrow fractions were successfully oxidised with 20 mM periodate and samples taken from different stages of the production process and analysed by GPC and native PAGE showed no change in the molecular weight and polydispersity.

Quantitative measurement of the oxidation state of CA was performed by ferricyanide ion reduction in alkaline solution to ferrocyanide (Prussian Blue) [Park and Johnson, 1949] using glucose as a standard. The oxidized CA was found to have a nearly 100 mol % of apparent aldehyde content as compared to native polymer. The results of quantitative assay of CA intermediates in the oxidation process using ferricyanide were consistent with the results of qualitative tests performed with 2,4 dinitrophenylhydrazine which gave a faint yellow precipitate with the native CA, and intense orange colour with the aldehyde containing forms of the polymer, resulting in an intense orange precipitate after ten minutes of reaction at room temperature.

The amination of the polymer was found to be 85% and the CA-NHS was positive for NHS. Further, the thiol content of the polymer was found to be 60%

The integrity of the internal alpha-2,8 linked Neu5Ac residues post periodate and borohydride treatment was analysed by GPC and the chromatographs obtained for the oxidised (CAO), amino CA (CA-NH$_2$), CA-NHS materials were compared with that of native CA. It was found (FIG. 9) that all CAs exhibit almost identical elution profiles, with no evidence that the various steps give rise to significant fragmentation or crosslinking (in case of CA-NHS) of the polymer chain. The small peaks are indicative of buffer salts.

Formation of the CA-GH conjugates was analysed by SEC-HPLC and SDS-PAGE. For the conjugation reaction with DSG the SDS-PAGE showed that there was no free GH remaining and that the conjugation reaction had gone to completion. This was confirmed by SEC-HPLC, whereby the CA-GH conjugates were eluted before the expected elution time of the free GH (a peak for free GH was not observed). On the other hand, analysis by SDS-PAGE of the conjugation reaction of CA-NH$_2$ to GH using BS$^3$ showed the presence of free GH, which was confirmed by SEC-HPLC with an elution peak around 70 minutes for the free protein. In addition, the SEC-HPLC enable the degree of conjugation to be determined at 53%.

The results (FIG. 10) show that in the conjugate lanes there are shifts in the bands which typically indicates an increase in mass indicative of a polysialylated-GH in comparison to GH. Further, GH conjugates were separated into different species by SEC-HPLC.

Example 3

Preparation of Iodoacetate Derivative of CA (CAI)

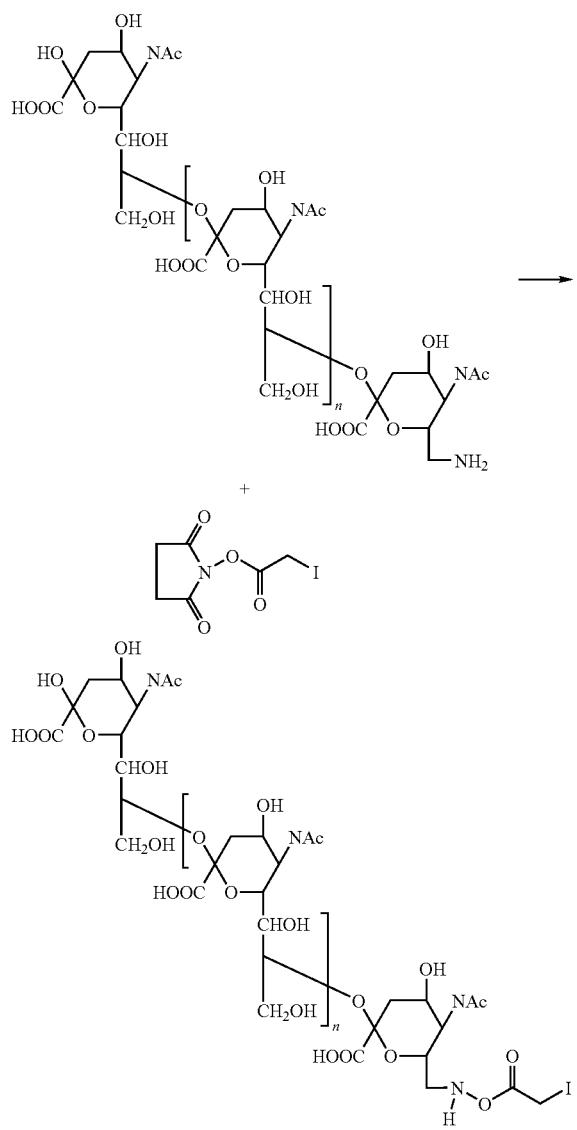

3.1 Synthesis

To 40 mg colominic acid amine (85 mol % amine) as (described in Reference Example 2) dissolved in 1 ml of PBS pH 7.4 was added 5 mg of N-succinimidyl iodoacetate (SIA). The mixture was left to react for 1 h at 25° C. in the dark, after which excess SIA was removed by gel filtration over a 5 ml Hightrap™ Desalting column(AP Bioscience) eluted with PBS. 0.5 ml fractions were collected from the column and samples from each fraction tested for colominic acid content (resorcinol assay) and reactivity with cysteine indicating Iodide (Ellman's Assay). Fractions positive for both iodide and CA were pooled.

3.2 Conjugation of CAI to β-galactosidase

To E. coli β-galactosidase (5.0 mg, $4.3 \times 10^{-8}$ mol) in 1 ml PBS 15 mg CAI was added ($6.59 \times 10^{-7}$ mol, 15 molar equiv). The tube was sealed wrapped in foil and the reaction was allowed to proceed at room temperature for 1 h whilst gently mixing. The resulting conjugate was analysed by SDS page and then purified according to accepted protocols to remove free CAI. Samples were assayed for polymer and protein content as outlined above.

Control reactions were carried out with CA as a negative control. All samples were analysed for β-gal activity as described below in section 3.3.

3.3 Assay for Enzyme Activity

Standards from 60 μg/ml to 3.75 μg/ml of fresh β-galactosidase were prepared in PBS. Sample of CAM-β-gal were diluted to 60 μg/ml in the same buffer. Enzyme activity of the conjugates was measured as follows: In a microtitre plate, to 100 μl of sample or standard was added 100 μl of All-in-One β-gal substrate (Pierce). The plate was incubated at 37° C. for 30 min and absorbance read at 405 nm. A calibration curve was prepared from the standards and the activity of the samples calculated from the equation for the linear regression of the curve.

3.4 Conclusions

Fractions 3-6 were positive for both polymer and iodoacetate and were pooled. The SDS page (4-12% Bis/Tris gel; FIG. 12) showed an increase in apparent molecular mass for samples incubated with the iodoacetamide derivative but not with control polymer. From the protein and polymer assays the conjugation ratio was determined to be 1.63 CAI:1 β-gal. β-gal activity was calculated to be 100.9% for the conjugated sample, compared to the free enzyme.

Example 4

Preparation of Colominic Acid Hydrazide (CAH)

4.1 Synthesis 50 mg of oxidised colominic acid (19 kDa) was reacted with 2.6 mg of hydrazine (liquid) in 400 μl of 20 mM sodium acetate buffer, pH 5.5, for 2 h at 25° C. The colominic acid was then precipitated with 70% ethanol. The precipitate was redissolved in 350 μl phosphate buffer saline, pH 7.4 and NaCNBH$_3$ was added to 5 mg/ml. The mixture was allowed to react for 4 h at 25° C., then frozen overnight. NaCNBH$_3$ and reaction by products were removed by gel permeation chromatography on a PD10 column packed with Sephadex G25, using 0.15M NH$_4$HCO$_3$ as the mobile phase. The fractions (0.5 ml each) were analysed by the TNBS assay (specific to amino groups; described earlier). Fractions 6, 7, 8 and 9 (the void volume fractions) had a strong singal, well above the background. The background was high due to the presence of the NH$_4^+$ ions. Fractions 6, 7, 8 and 9 also contained colominic acid. These four fractions, were freeze dried to recover the CA-hydrazide (CAH).

4.2 Preparation of Colominic Acid NHS (CA-NHS) and Colominic Acid-Protein Conjugates 10 mg of 19 kDa CA-hydrazide were reacted with 9 mg of BS$^3$ in 400 μl of PBS (pH 7.4) for 30 minutes at room temperature. The reaction mixture was applied to a PD-10 column packed with Sephadex G25 collecting 0.5 ml fractions. 0.1 mg of BSA was added to each fraction between 5 and 9. After 2 hours at room temperatures the fractions reacted with BSA. These samples were analysed by SDS-PAGE and SEC HPLC.

These fractions have little colominic acid. The colominic acid rich fractions (6 and 7) have a protein streak in addition to the bands present in the other samples and BSA, which is clear evidence of conjugation (FIG. 13).

The HPLC chromatogram of fraction 6 shows that there is a big shift in the retention time for conjugate as compared to free protein confirming conjugation (FIGS. 14a and b).

The BSA used contains impurities. The BSA peak is at 56 minutes (FIG. 14a).

In addition to peak at 56 minutes, there are larger species which are conjugates. There is a large peak at 80 minutes, which is the NHS released from the CA-NHS as it reacts with the protein. This cannot be free $BS^3$ as the CAH was passed through a gel permeation chromatography column, which will have removed. This strongly suggests that an NHS ester group was created on the CA molecule (FIG. 14b).

REFERENCES

Bendele, A., Seely, J., Richey, C., Sennello, G., Shopp, G., Renal tubular vacuolation in animals treated with polyethylene-glycol conjugated proteins, Toxicological sciences, 42 (1998) 152-157.

Beranova, M., Wasserbauer, R., Vancurova, D., Stifter, M., Ocenaskova, J., Mora, M., Biomaterials, 11 (2000) 521-524.

Brocchini, S., Polymers in medicine: a game of chess. Drug Discovery Today, 8, (2003) 111-112.

Carlsson, J., Drevin, H. And Axen, R., Biochem Journal, 173, (1978), 723-737.

Cheng T, Wu, M., Wu, P., Chern, J, Roffer, S R., Accelerated clearance of polyethylene glycol modified proteins by anti-polyethylene glycol IgM. Bioconjugate chemistry, 10 (1999) 520-528.

Cho, J. W. and Troy, F. A., PSA engineering: Synthesis of polysialylated neoglycosphingolipid by using the polytransferase from neuroinvasive E.coli K1, Proceedings of National Academic Sciences, USA, 91 (1994) 11427-11431.

Convers, C. D., Lejeune, L., Shum, K., Gilbert, C., Shorr, R. G. L, Physiological effect of polyethylene glycol conjugation on stroma-free bovine hemoglobin in the conscious dog after partial exchange transfusion, Artificial organ, 21 (1997) 369-378.

Dyer, J. R., Use of periodate oxidation in biochemical analysis, Methods of Biochemical Analysis, 3 (1956) 111-152.

Fernandes, A. I., Gregoriadis, G., Polysialylated asparaginase: preparation, activity and pharmacokinetics, Biochimica et Biophysica Acta, 1341 (1997) 26-34.

Fernandes, A. I., Gregoriadis, G., Synthesis, characterization and properties of polysialylated catalase, Biochimica et Biophysica Acta, 1293 (1996) 92-96.

Fernandes, A. I., Gregoriadis, G., The effect of polysialylation on the immunogenicity and antigenicity of asparaginase: implications in its pharmacokinetics, International Journal of Pharmaceutics, 217 (2001)215-224.

Fleury, P., Lange, J., Sur l'oxydation des acides alcools et des sucres par l'acid periodique, Comptes Rendus Academic Sciences, 195 (1932) 1395-1397.

Gregoriadis, G., Drug and vaccine delivery systems, in: PharmaTech, World Markets Research Centre Limited, London (2001) 172-176.

Gregoriadis, G., Fernandes, A., McCormack, B., Mital, M., Zhang, X, Polysialic acids: Potential for long circulating drug, protein, liposome and other microparticle constructs, in Gregoriadis, G and McCormack, B (Eds), Targeting of Drugs, Stealth Therapeutic Systems, Plenum Press, New York (1998) 193-205.

Gregoriadis, G., Fernandes, A, Mital, M., McCormack, B., Polysialic acids: potential in improving the stability and pharmacokinetics of proteins and other therapeutics, Cellular and Molecular Life Sciences, 57 (2000) 1964-1969.

Gregoriadis, G., McCormack, B., Wang, Z. Lifely, R., Polysialic acids: potential in drug delivery, FEBS Letters, 315 (1993) 271-276.

Hermanson, G. T., Bioconjugate techniques, Acadamic press, London, 1995.

Hreczuk-Hirst, D., Jain, S., Genkin, D., Laing, P., Gregoriadis, G., Preparation and properties of polysialylated interferon-α-2b, AAPS Annual Meeting, 2002, Toronto, Canada, M1056

Hunter, A. C, Moghimi, S. M., Therapeutic synthetic polymers: a game of Russian Roulette. Drug Discovery Today, 7 (2002) 998-1001.

Jain, S., Hirst, D. H., McCormack, B., Mital, M., Epenetos, A., Laing, P., Gregoriadis, G., Polysialylated insulin: synthesis, characterization and biological activity in vivo, Biochemica et. Biophysica Acta, 1622 (2003) 42-49.

Jain, S., Hirst, D. H., Laing, P., Gregoriadis, G., Polysialylation: The natural way to improve the stability and pharmacokinetics of protein and peptide drugs, Drug Delivery Systems and Sciences, 4(2) (2004) 3-9.

Jennings, H. J., Lugowski, C., Immunogenicity of groups A, B, and C meningococal polysaccharide tetanus toxoid conjugates, Journal of Immunology, 127 (1981) 1011-1018.

Lifely, R., Gilhert, A. S., Moreno, C. C., Sialic acid polysaccharide antigen of Neisseda meningitidis and Escherichia coli: esterification between adjacent residues, Carbohydrate Research, 94 (1981) 193-203.

Mital, M., Polysialic acids: a role for optimization of peptide and protein therapeutics, Ph.D. Thesis, University of London, 2004.

Muflenhoff, M., Ectehardt, M., Gerardy-Schohn, R., Polysialic acid: three-dimensional structure, biosynthesis and function, Current opinions in Structural Biology, 8 (1998) 558-564.

Park, J. T., Johnson, M. J., A submicrodetermination of glucose, Journal of Biological Chemistry, 181 (1949) 149-151.

Roth, J., Rutishauser, U., Troy, F. A. (Eds.), Polysialic acid: from microbes to man, Birkhäuser Verlag, Basel, Advances in Life Sciences, 1993.

Rutishauser, U., Polysialic acid as regulator of cell interactions in: R. U. Morgoles and R. K. Margalis (eds.), Neurobiology of Glycoconjugates, pp 367-382, Plenum Press, New York, 1989.

Satake, K., et. al., J. Biochem., 47, 654, 1960.

Shriner, R. L., Fuson, R. D. C., Curtin, D. Y., Morill, T. C., The Systematic Identification of Organic Compounds, $6^{th}$ ed., Wiley, New York, 1980.

Svennerholm, L., Quantitative estimation of sialic acid II: A colorimetric resorcinol-hydrochloric acid method, Biochimca et Biophysica Acta, 24 (1957) 604-611.

Troy, F. A. Polysialylation of neural cell adhesion molecules, Trends in Glycoscience and Glycotechnology, 2 (1990) 430-449.

Troy, F. A., Polysialylation: From bacteria to brain, Glycobiology, 2 (1992) 1-23.

The invention claimed is:
1. A compound of formula III or formula VIII

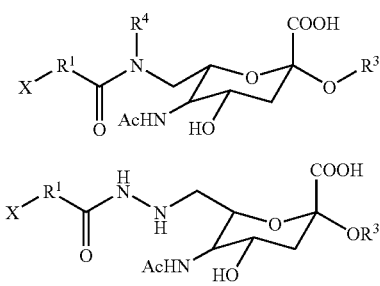

wherein X is a functional group selected from the group consisting of NHS-esters, vinyl sulfone, N-maleimido, N-iodoacetamido, orthopyridyl disulfide, hydroxy, protected hydroxyl, amino, protected amino, carboxyl, protected carboxyl, and azido groups;
$R^1$ is a linker;
$R^4$ is hydrogen or $C_{1-4}$ alkyl; and
$R^3$ is a mono-, di-, oligo- or poly-saccharide, a protein, a peptide, a lipid, a drug or a drug delivery system.

2. A compound according to claim 1 wherein $R^1$ is selected from the group consisting of alkanediyl, arylene, alkarylene, heteroarylene and alkylheteroarylene, any of which is optionally interrupted by carbonyl, ester, sulfide, ether, amide and/or amine linkages.

3. A compound according to claim 1 wherein $R^1$ is $C_3$-$C_6$ alkanediyl.

4. A compound according to claim 1 wherein $R^3$ is an oligo or poly-saccharide.

5. A compound according to claim 4 wherein $R^3$ is oligo- or poly-sialic acid.

* * * * *